(12) United States Patent
Brown

(10) Patent No.: US 10,135,216 B1
(45) Date of Patent: Nov. 20, 2018

(54) MONITORING METHOD AND APPARATUS FOR SURGICAL LASER FIBERS

(71) Applicant: Joe Denton Brown, Panama City Beach, FL (US)

(72) Inventor: Joe Denton Brown, Panama City Beach, FL (US)

(*) Notice: Subject to any disclaimer, the term of this patent is extended or adjusted under 35 U.S.C. 154(b) by 0 days.

(21) Appl. No.: 15/717,209

(22) Filed: Sep. 27, 2017

(51) Int. Cl.
*H01S 3/06* (2006.01)
*H01S 3/067* (2006.01)
*G01T 1/20* (2006.01)
*H01S 3/08* (2006.01)
*A61B 18/20* (2006.01)

(52) U.S. Cl.
CPC ........ *H01S 3/06737* (2013.01); *G01T 1/2012* (2013.01); *H01S 3/06733* (2013.01); *H01S 3/08086* (2013.01); *A61B 18/20* (2013.01)

(58) Field of Classification Search
CPC ............. H01S 3/06737; H01S 3/06733; H01S 3/08086; G01T 1/2012; A61B 18/20
See application file for complete search history.

(56) References Cited

U.S. PATENT DOCUMENTS

| | | | | |
|---|---|---|---|---|
| 4,712,096 A * | 12/1987 | Cholin | ................. | G02B 6/4206 340/590 |
| 5,438,860 A * | 8/1995 | Kawai | ..................... | E21B 12/02 408/16 |
| 6,259,517 B1 * | 7/2001 | Tedesco | ............. | G01M 11/3109 250/227.14 |
| 9,678,275 B1 | 6/2017 | Griffin | | |
| 2008/0188843 A1 | 8/2008 | Appling et al. | | |
| 2008/0283770 A1 * | 11/2008 | Takahashi | ............... | A61B 1/043 250/458.1 |
| 2013/0079467 A1 * | 3/2013 | Bruns | ...................... | C08K 9/08 525/54.1 |
| 2016/0187608 A1 * | 6/2016 | Brown | ................... | G01M 11/37 356/73.1 |
| 2016/0359288 A1 * | 12/2016 | Matsuoka | ............. | H01S 3/2383 |

OTHER PUBLICATIONS

Hutchens et al., "Hollow Steel Tips for Reducing Distal Fiber Burn-Back During Thulium Fiber Laser Lithotripsy"; Journal of Biomedical Optics 18(7), 078001 (Jul. 2013).

* cited by examiner

*Primary Examiner* — Marcus Taningco
(74) *Attorney, Agent, or Firm* — Bacon & Thomas, PLLC

(57) ABSTRACT

A method and apparatus for detecting excess absorption of therapeutic radiation at a bend in a fiber, and the possibility of imminent fiber failure, by monitoring stimulated radiation emission by phosphors in a coating of the fiber, the stimulated emission being caused by leakage of an aiming beam through the cladding into the coating. To accomplish the detection, a conventional monitoring method and equipment are modified to detect the absence of, or an interruption in, the stimulated emission, which is caused by separation of the coating from the cladding in the area of the bend as a result of the excess absorption.

2 Claims, 1 Drawing Sheet

MONITORING METHOD AND APPARATUS FOR SURGICAL LASER FIBERS

This application claims the benefit of U.S. Provisional Patent Appl. Ser. No. 62/400,306, filed Sep. 27, 2016.

BACKGROUND OF THE INVENTION

1. Field of the Invention

The invention relates to a method and apparatus for monitoring surgical laser fibers to early fiber failure resulting from over-absorption of high power therapeutic laser energy at a bend in the fiber.

2. Description of Related Art

Over-absorption of high power therapeutic laser energy at a bend in the fiber, which can lead to breakage of the fiber, has conventionally been difficult to detect. Such over-absorption can cause rapid overheating at the fiber bend, and sudden failure of the fiber, without being detected by conventional monitoring methods. As a result, the clinician has no warning of a potential failure until the failure actually occurs.

A conventional monitoring method is to monitor radiation emitted by phosphors in the coating of the fiber. An increase in emission of radiation by the phosphors indicates a defect in the fiber that causes excess leakage of an aiming beam into the cladding and coating of the fiber. The phosphors absorb radiation at a wavelength $\lambda_1$ characteristic of an aiming beam and emit radiation at a wavelength $\lambda_2$, the emitted radiation propagating back through the fiber so that it can be detected at the proximal end of the fiber, i.e., the end of the fiber that is closest to the laser source and away from the treatment site.

However, although an excess amount of stimulated radiation emission by the phosphors is indicative of a defect in the fiber, a certain amount of radiation is expected to be emitted by the phosphors, due to normal leakage of aiming beam radiation from the core into the cladding and coating of the fiber. This normal amount of radiation is conventionally disregarded, for example by providing a detection circuit that is only triggered by stimulated wavelength $\lambda_2$ emissions that are above a threshold.

A problem with the use of an aiming beam and stimulated phosphor emission to monitor the fiber arises when bending of the fiber causes excess amounts of energy from the main therapeutic laser to be absorbed at wavelength $\lambda_T$, but does not cause a corresponding increase in leakage of the aiming beam. Since the phosphors are stimulated by the aiming beam radiation $\lambda_1$, emission of radiation by the phosphors at wavelength $\lambda_2$ is not increased the excess absorption of therapeutic radiation at wavelength $\lambda_T$. As a result, the resulting overheating and possibility of imminent failure in the area of the bend will go undetected until failure actually occurs.

SUMMARY OF THE INVENTION

It is accordingly an objective of the invention to provide a method and apparatus of detecting overheating and imminent breakage of a fiber cause by over-absorption of therapeutic radiation at a bend in the fiber.

The method and apparatus of the invention involve monitoring of aiming-beam-induced emissions of radiation by phosphors in the fiber coating, but instead of just monitoring for increases in the emissions, the method and apparatus of the invention monitors for interruption in the emissions.

It has not previously been recognized that an interruption in the aiming-beam-induced phosphor emissions at wavelength $\lambda_2$ is indicative of overheating caused by over-absorption of the main therapeutic or treatment laser beam at wavelength $\lambda_T$. The explanation, discovered by the Inventor, is that, if a sufficient amount of therapeutic radiation is absorbed at a bend in the fiber, the coating will heat and expand, creating an air pocket or vacuum region between the coating and the cladding. This air space or vacuum changes an index of refraction outside the cladding such that the aiming beam radiation at wavelength $\lambda_1$ is totally internally reflected and the fiber stops emitting radiation of wavelength $\lambda_2$ in the affected region. As a result, the absence of radiation at wavelength $\lambda_2$ while lasing when the scope is deflected can be used to detect and prevent early fiber failure.

The invention thus provides a method and apparatus for detecting excess absorption of therapeutic radiation at a bend in a fiber, and the possibility of imminent fiber failure, by monitoring stimulated radiation emission by phosphors in a coating of the fiber. This can be achieved by modifying the conventional monitoring method and equipment such that an alarm or warning is triggered not only by detection of stimulated emission wavelengths that exceed a threshold, but also by detection of the absence of such stimulated emission wavelengths.

DETAILED DESCRIPTION OF THE PREFERRED EMBODIMENTS

Figure 1:
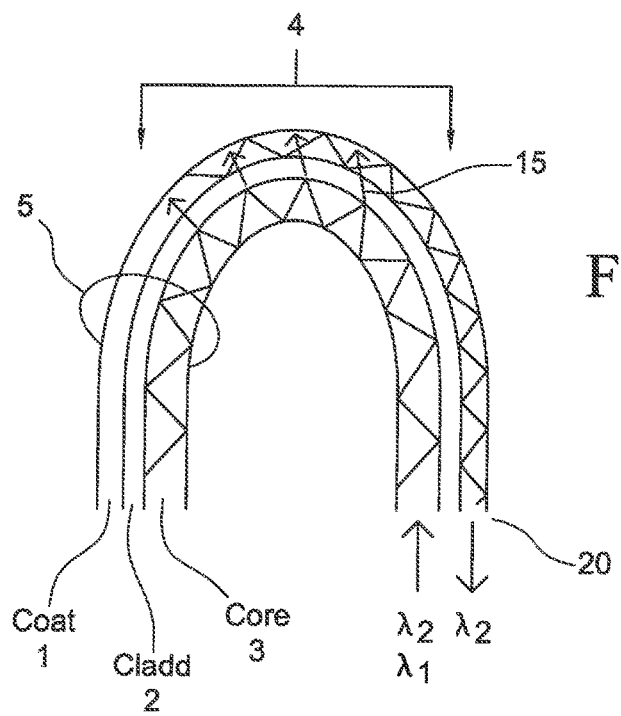
FIG. 1 illustrates one side of a bent fiber during normal delivery of therapeutic energy to a treatment site, with buffer removed.

FIG. 1 shows one side of a conventional optical fiber 5 of the type used in surgical procedures (for illustrative purposes, only the fiber core 3 and one side of the cladding 2 and coating 1 are shown, and the buffer is omitted). During a treatment procedure, therapeutic or treatment laser energy having a wavelength $\lambda_1$ is injected into a core 3 at a proximal end of the fiber 5 for delivery to a treatment site at the distal end of the fiber. Propagation of the therapeutic laser energy through the core is made possible by one or more of the cladding layers 2, which have an index of refraction that causes the therapeutic laser energy to undergo total internal reflection and therefore propagate along the length of the fiber.

In addition to the therapeutic laser, as shown in FIG. 1, an aiming beam is also injected into the proximal end of the fiber core, at the same time as the therapeutic laser energy. The aiming beam has a different wavelength $\lambda_2$ than the therapeutic laser. As described above, normal leakage of the aiming beam through the cladding of the fiber, indicated by reference number 15, will cause the aiming beam to stimulate phosphors in the coating 1 of the fiber, resulting in the emission by the phosphors of radiation at a wavelength at wavelength $\lambda_2$, which propagates back through the fiber and can be detected for example by doping a material of the coating.

Figure 2:
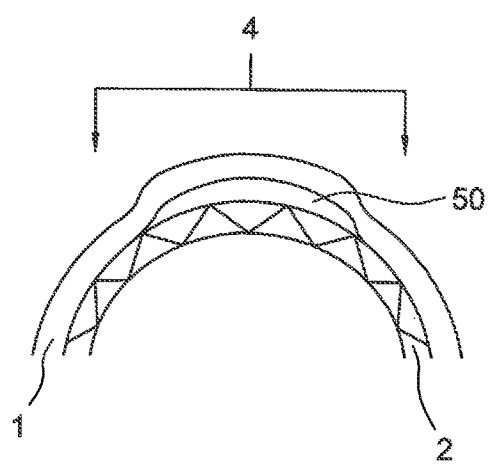
FIG. 2 illustrates an effect of excess therapeutic radiation absorption at the fiber bend.

At a bend 4 in the fiber, as illustrated in FIGS. 1 and 2, the angle of incidence of therapeutic laser energy incident on the fiber cladding is increased and not all of the laser energy is internally reflected. Eventually, if the bend is sharp enough, over-absorption and overheating of the therapeutic laser energy can occur. For a therapeutic laser wavelength of 2100 nm and a fully deflected endoscope of the type used in urological procedures, this may occur when the bent section is on the order of 10 mm.

Figure 3:
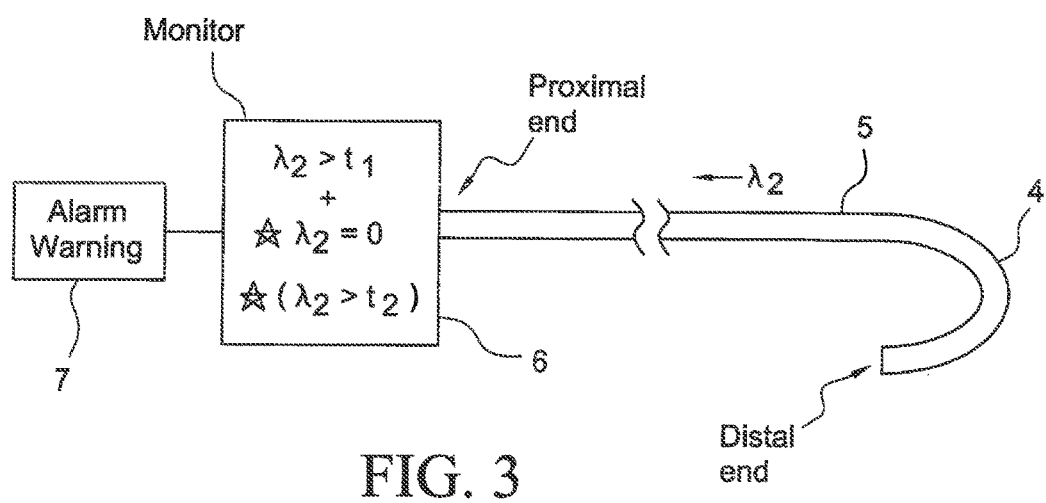
FIG. 3 is a schematic diagram of a preferred monitoring apparatus for implementing the monitoring method of the invention.

As shown in FIG. 3, a monitor is situated at the proximal end of the fiber 5. As is conventional, the monitor 6 detects emissions of stimulated phosphor emissions that exceed a threshold t1. 4. However, the monitor 6 is modified to also monitor lower levels of stimulated phosphor emissions that indicate normal leakage of the aiming beam into the coating, and to detect the absence of stimulated phosphor emissions, for example with respect to a second threshold t2. The absence of stimulated emissions occurs when, as shown in FIG. 2, the coating 3 is the area of the bend 4 expands as a result of overheating and separates from the cladding 2, leaving an air pocket or vacuum 50, and thereby interrupting the leakage of aiming beam radiation through the cladding into the coating.

Finally, as shown in FIG. 3, since the absence of stimulated emission radiation at wavelength $\lambda_2$ is indicative of overheating, a warning or alarm 7 may be triggered upon detection of the absence.

What is claimed is:

1. A method of detecting imminent fiber failure resulting from over-absorption of therapeutic laser radiation at a bend in a fiber, comprising the steps of:

carrying out a therapeutic laser procedure by causing therapeutic laser radiation to be delivered from a proximal end of the fiber to a distal end;

causing an aiming beam to be delivered through the fiber from the proximal end to the distal end;

monitoring for increases in stimulated emission by phosphors in a coating of the fiber;

when a fiber is bent, monitoring for interruptions in stimulated emission by phosphors in a coating of the fiber; and when an interruption of the stimulated emission is detected, providing an indication that over-absorption is occurring and that failure of the fiber may be imminent.

2. Apparatus for detecting imminent fiber failure resulting from over-absorption of therapeutic laser radiation at a bend in a fiber, comprising:

a monitor for monitoring, when a fiber is bent, stimulated emission by phosphors in a coating of the fiber, the emission being stimulated by leakage of an aiming beam through the cladding into the coating, wherein the monitor is adapted to not only detect increases in the stimulated emission, but also to detect, when the fiber is bent, an interruption in stimulated emission, and further comprising a warning device to provide an indication, upon detection of an interruption in stimulated emission, that over-absorption is occurring and that failure of the fiber may be imminent.

* * * * *